(12) United States Patent
Smith

(10) Patent No.: US 6,862,468 B2
(45) Date of Patent: Mar. 1, 2005

(54) SYSTEMS AND METHODS FOR MAGNETIC RESONANCE IMAGING ELASTOGRAPHY

(75) Inventor: Scott Raymond Smith, Chaska, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 224 days.

(21) Appl. No.: 09/967,773

(22) Filed: Sep. 28, 2001

(65) Prior Publication Data

US 2003/0065267 A1 Apr. 3, 2003

(51) Int. Cl.$^7$ .............................................. A61B 5/055
(52) U.S. Cl. ................................. 600/410; 324/309
(58) Field of Search ................. 600/410–411, 437–439, 600/421–425, 427, 459, 462–463, 466–467; 601/2–4; 324/307, 309, 318, 322

(56) References Cited

U.S. PATENT DOCUMENTS

| | | | |
|---|---|---|---|
| 5,178,147 A | 1/1993 | Ophir et al. ........... 128/660.01 |
| 5,233,994 A | 8/1993 | Shmulewitz ........... 128/661.08 |
| 5,293,870 A | 3/1994 | Ophir et al. ........... 128/660.01 |
| 5,474,070 A | 12/1995 | Ophir et al. ........... 128/660.01 |
| 5,590,653 A | * 1/1997 | Aida et al. .................... 600/411 |
| 5,792,055 A | * 8/1998 | McKinnon .................. 600/410 |
| 5,825,186 A | * 10/1998 | Ehman et al. .............. 324/309 |
| 5,899,858 A | 5/1999 | Muthupillai et al. ......... 600/410 |
| 6,019,725 A | 2/2000 | Vesely et al. ................ 600/447 |
| 6,246,895 B1 | * 6/2001 | Plewes ........................ 600/410 |

* cited by examiner

Primary Examiner—Eleni Mantis Mercader
(74) Attorney, Agent, or Firm—Orrick, Herrington & Sutcliffe LLP

(57) ABSTRACT

Systems and methods for generating Magnetic Resonance Imaging (MRI) elastographs of a region in a body are provided. A catheter, in accordance with one embodiment, comprises an elongated member, an acoustic transducer positioned near a distal end of the elongated member, and a Radio Frequency (RF) coil adjacent to the acoustic transducer. To generate an MRI elastograph of a region in a body, the acoustic transducer and the RF coil of the catheter are positioned at the desired region in the body. The acoustic transducer emits acoustic waves in the region of the body, and the RF coil detects RF signals emitted within the region of the body. The detected RF signals are outputted to an MRI receiver to generate the MRI elastograph of the region in the body.

54 Claims, 4 Drawing Sheets

SYSTEMS AND METHODS FOR MAGNETIC RESONANCE IMAGING ELASTOGRAPHY

BACKGROUND OF THE INVENTION

1. Field of the Invention

The present invention relates generally to Magnetic Resonance Imaging (MRI), and more particularly to systems and methods for generating an MRI elastograph of a region in a body using an acoustic transducer.

2. Background

A hydrogen atom, which has a single proton in its nucleus, exhibits a nuclear spin that produces a small magnetic moment vector. In the presence of a magnetic field, the magnetic moment vector of the hydrogen atom tends to align in the direction of the magnetic field. In addition, the nuclear spin of the hydrogen atom exhibits a resonance frequency, which is a function of the magnetic field strength and is approximately 42.85 MHz per Tesla.

The magnetic properties of the hydrogen atom are exploited in Magnetic Resonance Imaging (MRI) to generate an image of the interior of a human body. MRI images the interior of the body by measuring the hydrogen atom density at different positions inside the body. Because different tissues in the body have different hydrogen atom densities, MRI is able to translate the hydrogen atom density measurement into an image of the body.

MRI is used in a medical imaging technique called Magnetic Resonance Elastography (MRE) to image the relative stiffness of different regions inside the body. MRE stems from the importance of palpation in the diagnosis of certain cancers and tumors. Physicians typically use palpation to detect a tumor in the body by assessing the difference in stiffness between the tumor and the surrounding healthy tissue.

To image the relative stiffness of different regions inside a human body using MRE, an acoustic wave is applied to the body. The acoustic wave generates shear waves that propagate through the body. MRI is used to image the shear waves as they propagate through the body. The wavelength of the shear waves depends upon the stiffness of the body tissue through which they propagate. The wavelength is shorter in softer, more easily deformed, body tissue and is longer in harder body tissue. Several MRI images of the shear waves are taken at different acquisition times. The MRI wave images are then processed to generate an elastograph, which provides an image of the relative stiffness of different regions inside the body. The elastograph provides high contrast between soft and hard body tissue. This may be especially useful for the detection of tumors, which tend to be stiffer than the surrounding tissue.

Despite the advances in medical technology, further improvements in imaging tissues within the human body are required.

SUMMARY OF THE INVENTION

The present invention relates to systems and methods for generating an MRI image, such as an elastograph, of a region in a body using an acoustic transducer.

In a system built in accordance with the invention, a catheter comprises a flexible elongated member adapted to be inserted into a blood vessel. Alternatively, the catheter can be adapted for insertion into openings in the body, including those made by laparoscopic surgery. In this alternate configuration, the catheter is intended to image body tissue besides blood vessels. The catheter further comprises at least one acoustic transducer positioned near a distal end of the elongated member, and at least one RF coil positioned adjacent to the acoustic transducer. The catheter may be used in conjunction with a MRI system, such as that in FIG. 1, to produce an elastograph of the blood vessel or other body tissue near the blood vessel. In order to produce the elastograph, the elongated member of the catheter is inserted into the blood vessel of a patient. The acoustic transducer of the catheter is positioned at a desired region in the blood vessel. Also, the patient is placed within the magnet of the MRI system so that the blood vessel is positioned within the magnet of the MRI system. The acoustic transducer emits acoustic waves in the blood vessel, which may produce shear waves that propagate through the blood vessel and the surrounding tissue. MRI images of these shear waves propagating through the blood vessel and the surrounding tissue are then taken. To take these MRI images, the RF body coil(s) of the MRI system transmits magnetic pulses to cause the blood vessel and the surrounding tissue to emit RF signals. The RF coil of the catheter detects the emitted RF signals, and outputs the detected RF signals to an MRI receiver. The MRI receiver processes the detected RF signals to generate MRI images of the shear waves propagating through the blood vessel and the surrounding tissue. For example, several MRI images of the shear waves may be taken at different acquisition or sampling times. The MRI wave images are processed by the MRI receiver to produce an elastograph, which, as desired, may illustrate the relative stiffness of the blood vessel and the surrounding tissue.

In another embodiment, the acoustic transducer and RF coil are placed on a needle instead of the catheter. The needle according to this embodiment may be inserted into a region of the body, such as the liver or the brain, to generate an elastograph of the region.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
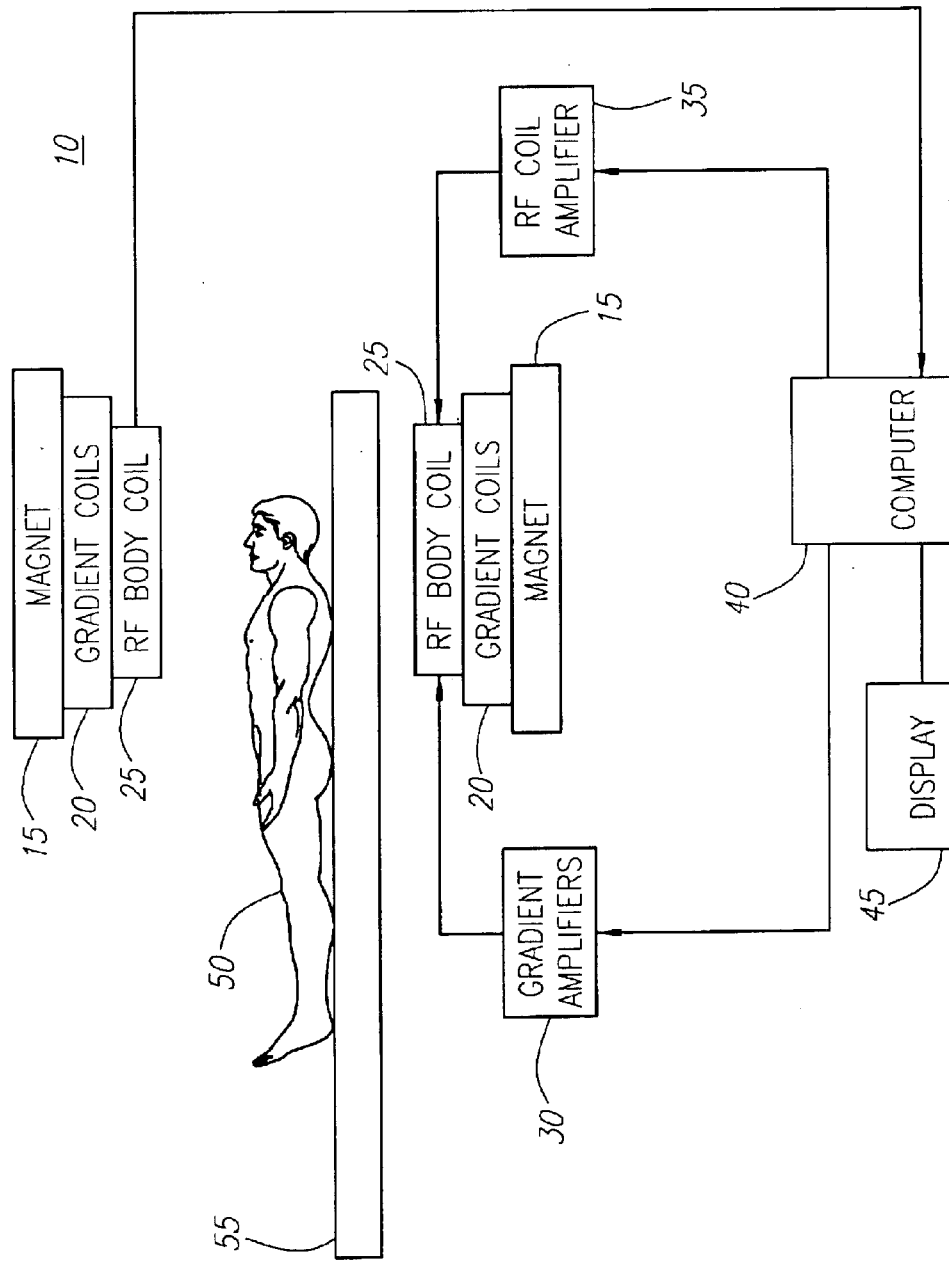
FIG. 1 illustrates a Magnetic Resonance Imaging (MRI) system of the prior art.

FIG. 1 shows an overview of a conventional MRI system 10 comprising a magnet 15, gradient coils 20, and a Radio Frequency (RF) body coil 25. The magnet 15 is typically made of a super-conducting material having a magnetic field strength of about 1.5 Tesla. The MRI system 10 further comprises gradient amplifiers 30, an RF coil amplifier 35, a computer 40 for controlling the MRI system 10, and a display 45 for displaying MRI images.

The gradient amplifiers 30 are coupled between the computer 40 and the gradient coils 20, and are used to amplify control signals from the computer 40 to the gradient coils 25. The RF coil amplifiers 35 are coupled between the computer 40 and the RF body coil 25, and are used to amplify signals from the computer 40 to the RF body coil 20.

To image inside a human body using the MRI system 10, a patient 50 is placed on a table 55, which can slide to a position within the magnet 15 and the RF body coil 25. The MRI system 10 is capable of imaging a volume of the patient's body located within the magnet 15 and the RF body coil 25. The gradient coils 20 apply a linear magnetic field gradient to the magnetic field of the magnet 15. The computer 40 controls the slope and/or direction of the magnetic field gradient applied by the gradient coils 20. The magnetic field gradient causes hydrogen atoms at different positions inside the human body to exhibit slightly different resonance frequencies. The computer 40 then transmits a pulse signal to the RF body coil 25 via the RF coil amplifiers 35. The pulse signal causes the RF body coil 25 to transmit a magnetic pulse through the body in a direction that rotates the magnetic moment vectors of the hydrogen atoms away from the magnetic field of the magnet 15, thereby exciting the hydrogen atoms to a higher energy state.

When the magnetic pulse ceases, the hydrogen atoms relax back to a lower energy state in a process called Free Induction Decay (FID). During FID, the hydrogen atoms emit RF signals at their resonance frequencies. Due to the applied magnetic field gradient of the gradient coils 20, the hydrogen atoms at different positions inside the body emit RF signals at slightly different resonance frequencies. The RF body coil 25 detects the emitted RF signals, and outputs the detected RF signals to the computer 40. The computer 40 processes the detected RF signals to generate an image of the interior of the body, which is displayed on the display 45. The computer 40 is able to determine at which position each detected RF signal was emitted by correlating the resonance frequency of the RF signal with information about the applied magnetic field gradient. The MRI system 10 typically takes several measurements at different magnetic field gradients to generate an MRI image.

To better image a localized region of a human body, a small surface RF coil (not illustrated) may be used in conjunction with the MRI system 10 in FIG. 1. In this arrangement, the small surface RF coil is positioned near a localized region of the human body. The RF body coil 25 then transmits a magnetic pulse through the localized region of the body to cause the localized region to emit RF signals. The RF body coil 25 may also have the ability to receive RF signals if desired. The small surface RF coil detects the emitted RF signals within the localized region. An advantage of using a small surface RF coil to detect the emitted RF signals is that it typically has a better Signal-to-Noise Ratio (SNR) than the RF body coil 25.

Figure 2:
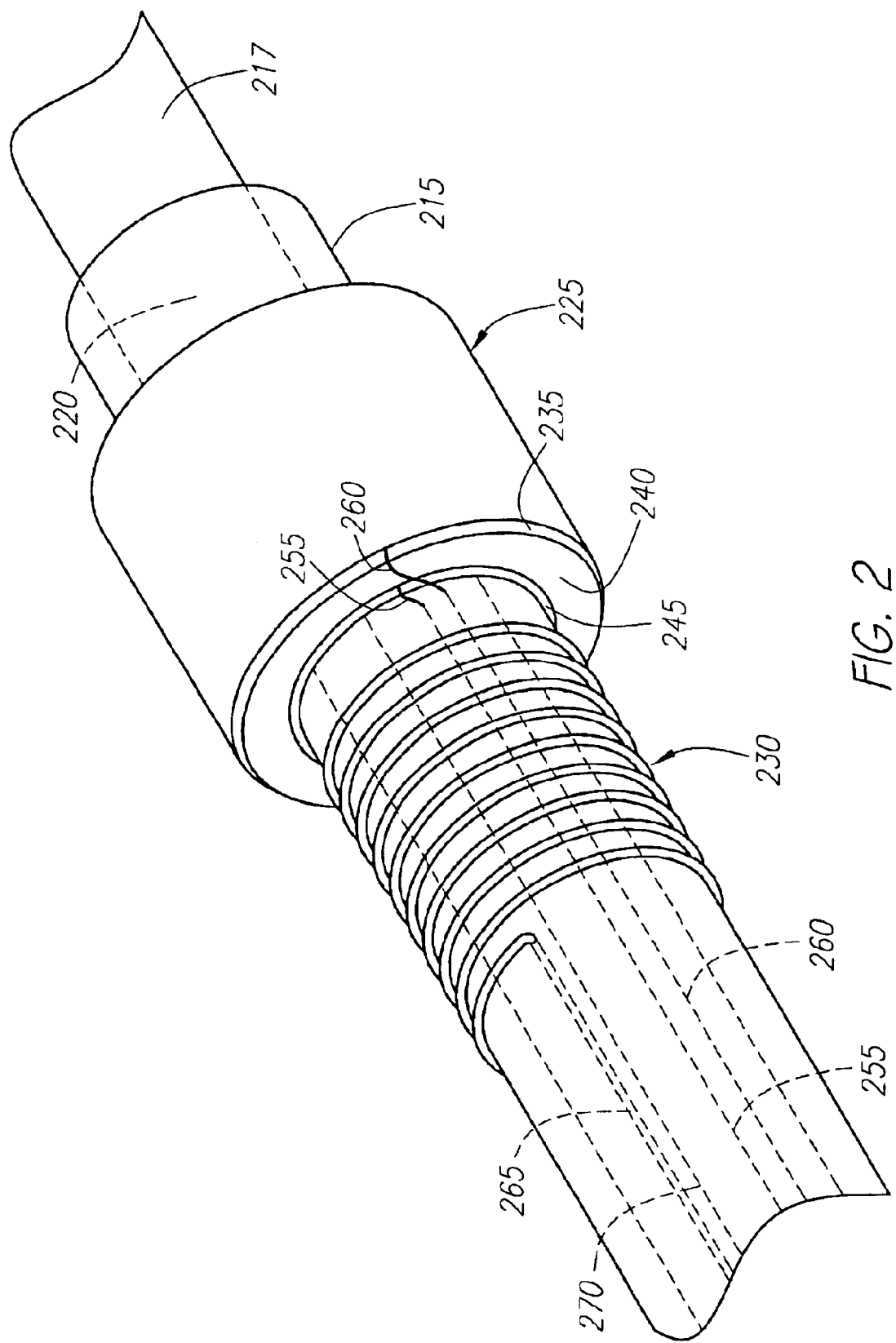
FIG. 2 is a perspective view of an example embodiment of a catheter for use with a MRI system.

FIG. 2 shows a perspective view of an example embodiment of a catheter 210 for use with a MRI system. The catheter 210 comprises a flexible elongated member 215. The elongated member 215 is preferably made of a flexible material including, but not limited to, nylon, polyurethane, polyethylene, and the like. The elongated member 215 may be 100 centimeters or more in length and has an elongated lumen 220 running longitudinally therethrough. A guide wire 217 is provided for guiding the catheter 210 along the path of a blood vessel. The guide wire 217 may be coupled to the distal end of the elongated member 215, or run through the elongated lumen 220, or another lumen.

The catheter 210 also comprises an acoustic transducer 225, e.g., an ultrasound transducer, located near the distal end of the elongated member 215 for transmitting acoustic waves. A polymer (not shown) is preferably coated on the acoustic transducer 225 to provide an acoustic matching layer between the transducer 225 and fluids in the body such as in a blood vessel. The catheter 210 further comprises a Radio Frequency (RF) coil 230, preferably wound around the elongated member 215 and adjacent to the acoustic transducer 225. The RF coil 230 may be made of copper wiring, for example. In addition, the RF coil 265 may be covered by a protective coating (not shown), such as a polymer used to coat the transducer 225. Leads 255, 260, 265, 270, or coaxial cable, are provided to run through the elongated member lumen 220. Each end of the RF coil 230 is coupled to one of the leads or coaxial cable. Of course, individual aspects of the catheter 210 can be altered as desired. Features known in the art can certainly be added without departing from the scope of the invention. For example, the catheter can have a single lumen or multiple lumens, an inflatable balloon or other device coupled to the catheter, a single transducer or multiple transducers, or a rotating or fixed transducer 225. The catheter can have its leads embedded within the catheter walls, or disposed within a separate lumen.

Figure 3:
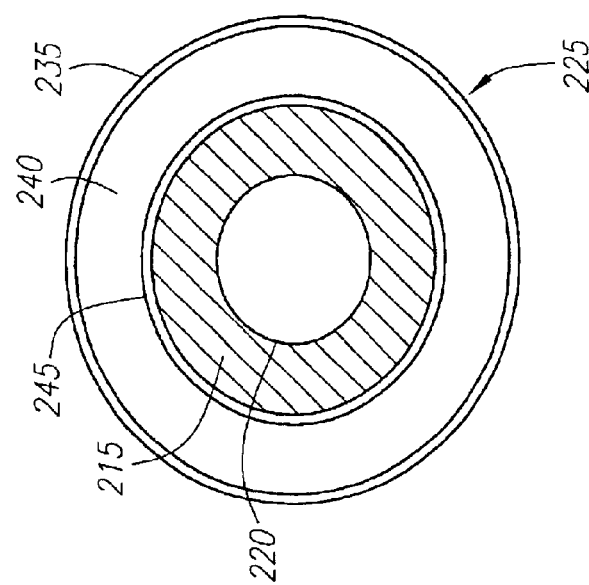
FIG. 3 is a cross-sectional view of an example embodiment of an acoustic transducer for a catheter for use with an MRI system.

FIG. 3 shows a cross-sectional view of an example embodiment of the acoustic transducer 225 taken along a plane perpendicular to the axis of the elongated member 215. In this example embodiment, the acoustic transducer 225 comprises an inner cylindrical conductive layer 245 surrounding the elongated member 215, a piezoelectric crystal layer 240 surrounding the inner conductive layer 245, and an outer cylindrical conductive layer 235 surrounding the piezoelectric crystal layer 240. The inner and outer conductive layers 245, 235 may each be a few microns thick, e.g., 2 microns, and may each be made of aluminum. The inner and outer conductive layer 245, 235 are each coupled to a lead 260, 255, respectively, or to a coaxial cable running through the elongated member lumen 220. The construction of the above-described acoustic transducer 225 is well known in the art and is typically used to construct ultrasound transducers for passivating plaque in blood vessels and facilitating the diffusion of medication into blood vessels. Such ultrasound transducers may also be used in balloon angioplasty to clear obstructions in blood vessels. Of course, other types of transducers may be used, such as those made with a capacitor, magnetic induction coil, or opto-acoustic device, as is well known in the art.

Figure 4:
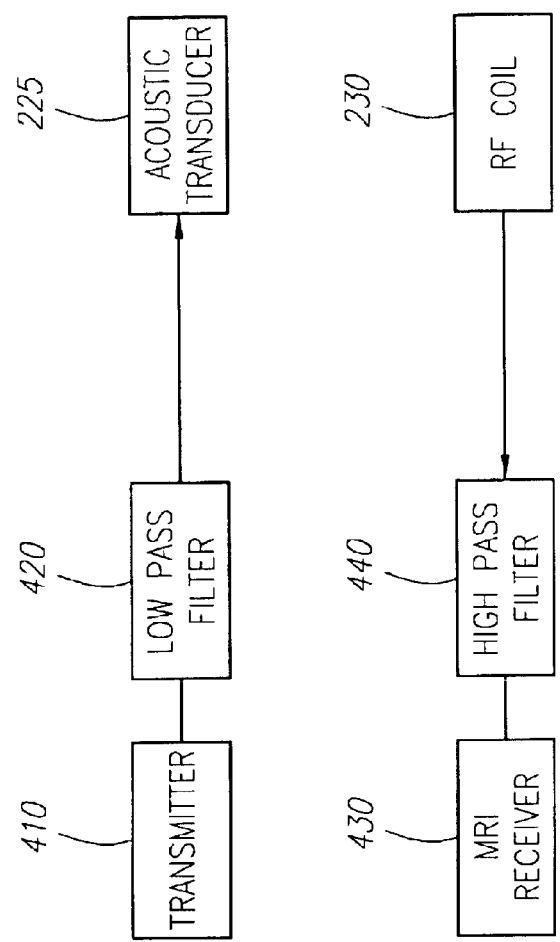
FIG. 4 is a block diagram illustrating external systems coupled to an acoustic transducer and a Radio Frequency (RF) coil of the catheter for use with an MRI system.

FIG. 4 is a block diagram illustrating examples of external systems which may be coupled to the acoustic transducer 225 and the RF coil 230. The acoustic transducer 230 is coupled to a transmitter 410 and a low pass filter 420 via leads 255, 260. The transmitter 410 transmits a pulsating excite signal to the acoustic transducer 225 through the low pass filter 420. The low pass filter 420 is constructed to pass signals within a frequency range of the excite signal. The excite signal from the transmitter 410 modulates the thickness of the piezoelectric crystal layer 240 causing the acoustic transducer 225 to emit acoustic wave. Typically, the thickness of the piezoelectric crystal layer 240 and the frequency of the excite signal are chosen to achieve a desired acoustic frequency of the acoustic wave. The acoustic frequency of the wave may be changed as desired.

The RF coil 230 is coupled to an MRI receiver 430 and a high pass filter 440 via leads 265, 270. The RF coil 230 detects RF signals in the vicinity of the acoustic transducer 225. The detected RF signals are outputted to the MRI receiver 430 through the high pass filter 440. The high pass filter 440 is constructed to pass signals above a frequency of, for example, a few tens of megahertz, e.g., 64 MHz, to the MRI receiver 430. The MRI system uses the detected RF signals to generate an MRI image of a region surrounding the acoustic transducer 225.

The catheter 210 may be used in conjunction with a MRI system such as MRI system 10 in FIG. 1 to produce an elastograph of a blood vessel, or of nearby tissues. In such a method, the elongated member 215 of the catheter 210 is inserted into the blood vessel of a patient. The acoustic transducer 225 is then positioned at a desired region in the blood vessel. Also, the patient is placed within the magnet 15 of the MRI system 10 such that the blood vessel is positioned within the magnet 15 of the MRI system 10. The transmitter 410 transmits an excite signal to the acoustic transducer 225 which causes the acoustic transducer 225 to emit acoustic waves of a predetermined frequency in the blood vessel. The acoustic waves may have a frequency of, for example, a few tens of kilohertz, e.g., 20 kHz. The acoustic waves may produce shear waves that propagate through the blood vessel and the surrounding tissue. Alternatively, the catheter can be adapted for insertion into openings in the body, including natural openings and those made by laparoscopic surgery. In this alternate configuration, the catheter is intended to image body tissue besides blood vessels.

The RF body coil 25 of the MRI system 10 transmits magnetic pulses to the human body in order to cause the blood vessel and the surrounding tissue to emit RF signals. The RF coil 230 of the catheter 210 detects the emitted RF signals, and outputs the detected RF signals to the MRI receiver 430. The MRI receiver 430 processes the detected RF signals to generate an MRI image of the shear waves propagating through the blood vessel and/or the surrounding tissue. Several MRI images of the shear waves may be taken at different acquisition or sampling times. The MRI wave images are processed by the MRI receiver 430 to generate an elastograph showing, for example, the relative stiffness of the blood vessel and the surrounding tissue.

The resulting elastograph may be useful for the detection of atherosclerosis plaque in the blood vessel. Atherosclerosis plaque is characterized by an atheroma with a large lipid pool covered by a thin fibrous cap. Because atherosclerosis plaque tends to be softer than the surrounding blood vessel wall, the elastograph can provide a sharp contrast between the atherosclerosis plaque and the blood vessel wall, and thereby enhanced detection of the atherosclerosis plaque.

Figure 5:
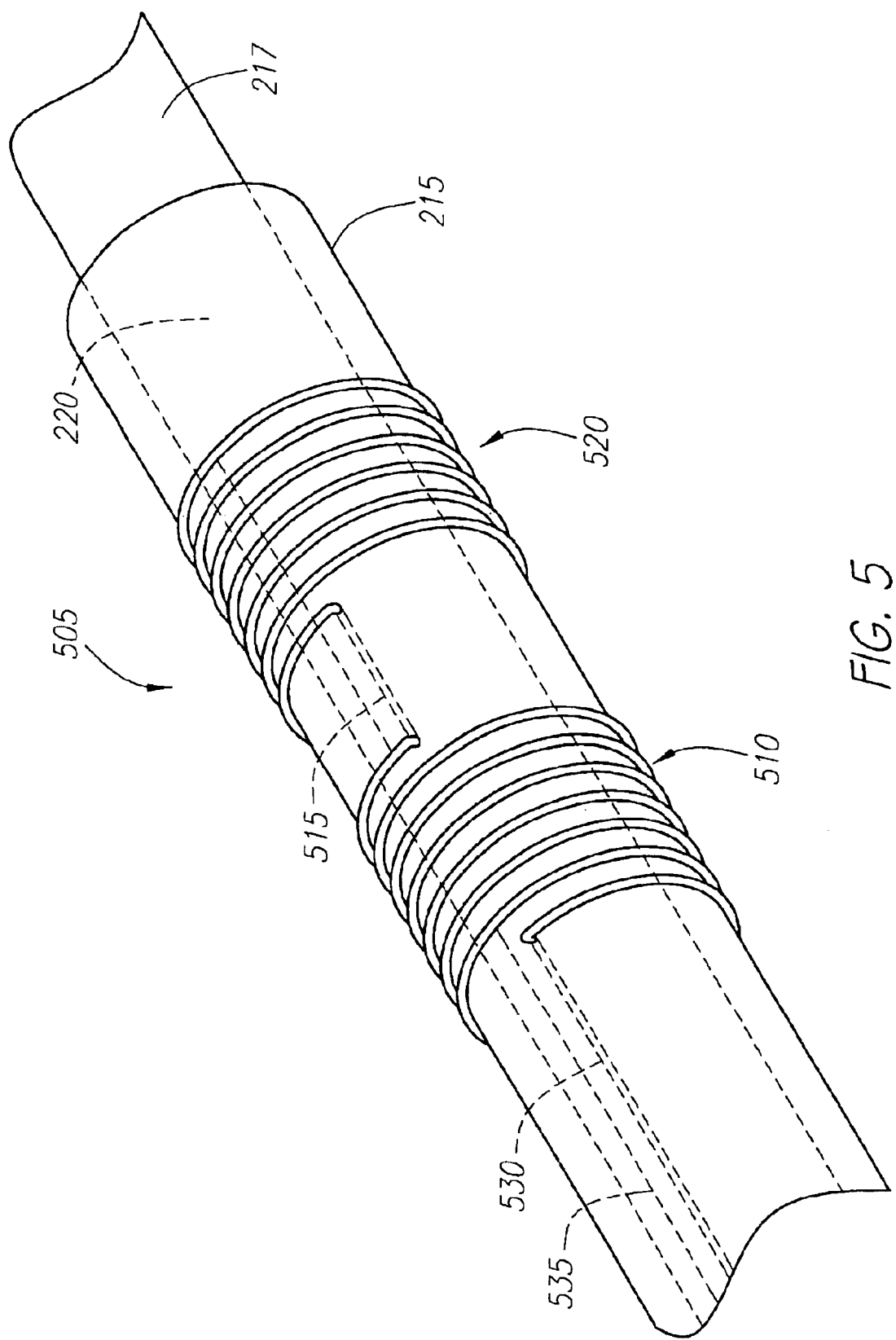
FIG. 5 is a perspective view of an example embodiment of an opposed solenoid RF coil for a catheter.

FIG. 5 shows an example embodiment of an opposed solenoid RF coil 505 for a catheter. The opposed solenoid RF coil 505 comprises a first coil 510 wound around the elongated member 215 in one direction and a second coil 520 wound around the elongated member 215 in the opposite direction. For example, if the first coil 510 is wound in a left-hand direction, then the second coil 520 is wound in a right-hand direction, or vice versa. In this particular example, the first and second coils 510, 520 are spaced apart so that the acoustic transducer 225 can be placed between the first and second coils 510, 520 on the elongated member 215. For ease of illustration, the acoustic transducer 225 is not shown in FIG. 5, although it is to be understood that the acoustic transducer 225 is located between the first and second coils 510, 520.

One end of the first coil 510 is coupled to a lead 530 or coaxial cable running through the elongated member lumen 220. The other end of the first coil 510 is coupled to the second coil 520. The connection between the two coils, preferably, runs through the elongated member lumen 220 in order to avoid contact with the inner conductive layer 245 of the acoustic transducer 225 (not shown in FIG. 5). The other end of the second coil 520 is coupled to a lead 535 or coaxial cable running through the elongated member lumen 220.

The opposed solenoid RF coil 505 is sensitive to RF signals in the region between the first and second coils 510, 520, where the acoustic transducer 225 is located. Therefore, the opposed solenoid RF coil 505 may be used to provide enhanced detection of RF signals in the vicinity of the acoustic transducer 225.

In another embodiment, the acoustic transducer 225 and RF coil 230 may be placed on a needle instead of the elongated member 215 of the catheter 210. The needle may be hollow for running leads therethrough to couple the transducer 225 and the RF coil 230 to external systems. The needle according to this embodiment may be inserted into a region of the body, such as the liver or the brain, to provide an elastograph of the region. This may be useful for the detection of tumors, which tend to be stiffer than the surrounding tissue.

While various embodiments of the application have been described, it will be apparent to those of ordinary skill in the art that many embodiments and implementations are possible that are within the scope of the present invention. For example, those skilled in the art will appreciate that a plurality of acoustic transducers may be placed on the elongated member 215 of the catheter 210 in order to vary the acoustical wave pattern emitted from the catheter 210. As another example, the plurality of acoustic transducers may be used in a focused or a phase array. Therefore, the invention is not to be restricted or limited except in accordance with the following claims and their equivalents.

What is claimed is:

1. A catheter system, having a catheter adapted to be inserted into a human body, comprising:
   an elongated member;
   an acoustic transducer coupled to the elongated member;
   a Radio Frequency (RE) signal detector on the elongated member adjacent to the acoustic transducer; and
   a receiver adapted to receive signals from the RF signal detector, wherein the receiver is configured to process the signals to generate an elastograph.

2. The catheter of claim 1, wherein the acoustic transducer comprises a piezoelectric crystal.

3. The catheter of claim 1, wherein the acoustic transducer comprises:
   an inner cylindrical conductive layer surrounding the elongated member;
   a piezoelectric crystal layer surrounding at least part of the inner cylindrical conductive layer; and
   an outer cylindrical conductive layer surrounding the piezoelectric crystal.

4. The catheter of claim 1, wherein the RF signal detector comprises an RF coil.

5. The catheter of claim 4, wherein the acoustic transducer comprises a piezoelectric crystal.

6. The catheter of claim 4, wherein the RF coil is wound around the elongated member.

7. The catheter of claim 1, wherein the elongated member has an elongated lumen running longitudinally therethrough.

8. The catheter of claim 7, wherein the RF signal detector comprises an RF coil and the catheter further comprises two leads running through the elongated lumen, each lead being coupled to one end of the RF coil.

9. The catheter of claim 7, further comprising a guide wire running through the elongated lumen.

10. The catheter of claim 7, further comprising a second lumen running through the elongated member.

11. The catheter of claim 1, wherein the RF signal detector further comprises:
 a first RF coil wound in a first direction; and
 a second RF coil coupled to the first RF coil and wound in a second direction opposite of the first direction.

12. The catheter of claim 11, wherein the acoustic transducer is positioned between the first RF coil and the second RF coil.

13. The catheter of claim 1, wherein the RF signal detector is coupled to a Magnetic Resonance Imaging (MRI) receiver.

14. The catheter of claim 1, wherein the acoustic transducer is mounted to the elongated member.

15. The catheter of claim 14, further comprising a second acoustic transducer.

16. The catheter of claim 1, wherein the acoustic transducer is rotatably coupled to the elongated member.

17. The catheter of claim 1, wherein the acoustic transducer comprises a capacitor.

18. The catheter of claim 1, wherein the acoustic transducer comprises a magnetic coil.

19. The catheter of claim 1, wherein the acoustic transducer comprises an opto-acoustic device.

20. A medical probe system, comprising:
 a needle adapted to be inserted into a body;
  an acoustic transducer coupled to the needle;
  a Radio Frequency (RF) signal detector coupled to the needle adjacent to the acoustic transducer; and
  a receiver adapted to receive signals from the RF signal detector, wherein the receiver processes the signals to generate an elastograph.

21. The medical probe of claim 20, wherein the acoustic transducer comprises a piezoelectric crystal.

22. The medical probe of claim 20, wherein the acoustic transducer comprises:
 an inner cylindrical conductive layer surrounding the needle;
 a piezoelectric crystal layer surrounding at least a part of the inner cylindrical conductive layer; and
 an outer cylindrical conductive layer surrounding the piezoelectric crystal.

23. The medical probe of claim 20, wherein the RF signal detector comprises an RF coil.

24. The medical probe of claim 23, wherein the acoustic transducer comprises a piezoelectric crystal.

25. The medical probe of claim 23, wherein the RF coil is wound around the needle.

26. The medical probe of claim 20, wherein the RF signal detector further comprises:
 a first RF coil wound around the needle in a first direction; and
 a second RF coil coupled to the first RF coil and wound around the needle in a second direction opposite to the first direction.

27. The medical probe of claim 26, wherein the acoustic transducer is positioned between the first RF coil and the second RF coil.

28. The medical probe of claim 20, wherein the RF signal detector is coupled to a Magnetic Resonance Imaging (MRI) receiver.

29. The medical probe of claim 20, wherein the acoustic transducer is mounted to the needle.

30. The medical probe of claim 20, wherein the acoustic transducer is rotatably coupled to the needle.

31. The medical probe of claim 20, further comprising a second acoustic transducer.

32. The medical probe of claim 20, further comprising elongated lumen running through the needle.

33. A method for producing an elastograph of a region inside a body, comprising:
 (a) transmitting acoustic waves to the region;
 (b) allowing the transmitted acoustic waves to propagate through the region;
 (c) detecting RF signals emitted from the region using an RF signal detector located inside the region;
 (d) using Magnetic Resonance Imaging (MRI) and processing the detected RF signals to generate an image of the acoustic waves propagating through the region;
 (e) repeating at least steps (c) and (d) to generate a second image; and
 (f) processing the generated images to produce an elastograph of the region.

34. The method of claim 33, wherein the step of transmitting acoustic waves to the region includes the step of transmitting acoustic waves from an acoustic transducer located inside the region.

35. The method of claim 33, wherein the step of detecting RF signals emitted from the region using an RF signal detector located inside the region includes the step of using an RF signal detector with an RF coil.

36. The method of claim 33, further comprising the steps of:
 applying a magnetic field gradient to the region; and
 transmitting magnetic pulses to the region to cause the emissions of RF signals from the region.

37. The method of claim 33, wherein the step of transmitting acoustic waves to the region includes transmitting acoustic waves that have a frequency of approximately 20 KHz.

38. The method of claim 33, wherein the step of detecting RF signals emitted from the region using an RF signal detector located inside the region includes detecting RF signals that have a frequency of approximately 64 MHz.

39. The method of claim 33, wherein the step of transmitting acoustic waves to the region includes transmitting acoustic waves to a blood vessel.

40. The method of claim 33, wherein the step of transmitting acoustic waves to the region includes transmitting acoustic waves to a naturally occurring opening in the human body.

41. The method of claim 33, wherein the step of transmitting acoustic waves to the region includes transmitting acoustic waves to an opening that was created by surgery in the human body.

42. The method of claim 33, wherein the step of detecting RF signals emitted from the region using an RF signal detector located inside the region includes the step of using an RF signal detector comprising a first RF coil wound around the needle in a first direction and a second RF coil coupled to the first RF coil and wound around the needle in a second direction opposite to the first direction.

43. The method of claim 33, wherein the step of transmitting acoustic waves to the region includes the step of transmitting acoustic waves from an acoustic transducer.

44. The method of claim 42, wherein the step of transmitting acoustic waves to the region includes the step of transmitting acoustic waves from an acoustic transducer.

45. The method of claim 44, wherein the step of transmitting acoustic waves to the region includes the step of transmitting acoustic waves from an acoustic transducer that is positioned between the first RF coil and the second RF coil.

46. A method for producing an elastograph of a region inside a body, comprising:

transmitting acoustic waves from an acoustic transducer located inside the region;

generating at least two Magnetic Resonance Imaging (MRI) images of the acoustic waves propagating through the region; and processing the generated images to produce an elastograph of the region.

47. The method of claim 46, wherein transmitting acoustic waves from an acoustic transducer located inside the region includes transmitting acoustic waves to a blood vessel and the acoustic transducer is coupled to a catheter located inside the blood vessel.

48. The method of claim 47, wherein the transmitting acoustic waves from an acoustic transducer located inside the region includes transmitting acoustic waves from an acoustic transducer that comprises a piezoelectric crystal.

49. The method of claim 47, wherein transmitting acoustic waves from an acoustic transducer located inside the region further comprises using an acoustic transducer having a capacitor.

50. The method of claim 47, wherein transmitting acoustic waves from an acoustic transducer located inside the region further comprises using an acoustic transducer having a magnetic coil.

51. The method of claim 47, wherein transmitting acoustic waves from an acoustic transducer having an opto-acoustic device.

52. The method of claim 46 further comprising the step of detecting RF signals emitted from the region.

53. The method of claim 52, wherein the step of detecting RF signals includes using an RF signal detector.

54. The method of claim 53, wherein the step of detecting RF signals includes using the RF signal detector having a first RF coil wound around the needle in a first direction and a second RF coil coupled to the first RF coil and wound around the needle in a second direction opposite to the first direction.

* * * * *